United States Patent
Bruder et al.

(10) Patent No.: US 7,016,455 B2
(45) Date of Patent: Mar. 21, 2006

(54) IMAGING TOMOGRAPHY APPARATUS WITH AT LEAST TWO RADIATOR-DETECTOR COMBINATIONS

(75) Inventors: Herbert Bruder, Hoechstadt (DE); Thomas Flohr, Uehlfeld (DE); Karlheinz Pauli, Neunkirchen (DE); Juergen Simon, Forchheim (DE)

(73) Assignee: Siemens Aktiengesellschaft, Munich (DE)

( * ) Notice: Subject to any disclaimer, the term of this patent is extended or adjusted under 35 U.S.C. 154(b) by 70 days.

(21) Appl. No.: 10/762,795

(22) Filed: Jan. 22, 2004

(65) Prior Publication Data

US 2005/0089134 A1  Apr. 28, 2005

(30) Foreign Application Priority Data

Jan. 22, 2003  (DE) ............................... 103 02 565

(51) Int. Cl.
*H05G 1/64* (2006.01)
*H05G 1/70* (2006.01)

(52) U.S. Cl. .......................................... 378/9; 378/197
(58) Field of Classification Search .................... 378/9, 378/65, 92, 147, 150, 151, 152, 156, 157, 378/158, 196, 197, 198
See application file for complete search history.

(56) References Cited

U.S. PATENT DOCUMENTS

| | | | |
|---|---|---|---|
| 4,196,352 A | 4/1980 | Berninger et al. | 378/7 |
| 4,303,830 A * | 12/1981 | Heinzelmann et al. | 378/9 |
| 4,371,976 A * | 2/1983 | Wagner | 378/16 |
| 4,384,359 A | 5/1983 | Franke | 378/9 |
| 4,991,190 A | 2/1991 | Mori | 378/9 |
| 5,724,400 A * | 3/1998 | Swerdloff et al. | 378/65 |
| 5,966,422 A | 10/1999 | Dafni et al. | 378/9 |
| 6,198,790 B1 | 3/2001 | Pflaum | 378/9 |
| 6,298,117 B1 | 10/2001 | Hampel et al. | 378/150 |
| 6,421,412 B1 | 7/2002 | Hsieh et al. | 378/9 |
| 6,438,202 B1 * | 8/2002 | Olivera et al. | 378/65 |
| 6,445,761 B1 | 9/2002 | Miyazaki et al. | 378/8 |
| 6,633,627 B1 * | 10/2003 | Horiuchi | 378/156 |
| 6,819,738 B1 * | 11/2004 | Hoffman | 378/19 |
| 6,842,502 B1 * | 1/2005 | Jaffray et al. | 378/65 |
| 6,876,719 B1 * | 4/2005 | Ozaki | 378/7 |
| 2003/0076920 A1 * | 4/2003 | Shinno et al. | 378/4 |
| 2003/0076927 A1 * | 4/2003 | Nakashima et al. | 378/65 |
| 2004/0213371 A1 * | 10/2004 | Bruder et al. | 378/9 |

* cited by examiner

Primary Examiner—Allen C. Ho
(74) Attorney, Agent, or Firm—Schiff Hardin LLP

(57) ABSTRACT

An imaging tomography apparatus, in particular an x-ray computed tomography apparatus, has two acquisition systems capable of rotating around a common rotation axis. Each of the acquisition systems has a radiator as well as a detector. The maximum measurement fields scanned by the two acquisition systems given rotation around the rotation axis are of different sizes, or can be adjusted to different sizes. In particular, the lengths of both detectors measured in the azimuthal direction—are of different sizes. The tomography apparatus can be fashioned to scan the entire body cross-section of an examination subject or of a patient with conventional temporal resolution, and to scan detail region, such as a heart region, with an increased temporal resolution or accelerated data acquisition rate in comparison to a device with only one acquisition system.

37 Claims, 4 Drawing Sheets

IMAGING TOMOGRAPHY APPARATUS WITH AT LEAST TWO RADIATOR-DETECTOR COMBINATIONS

BACKGROUND OF THE INVENTION

1. Field of the Invention

The present invention concerns an imaging tomography apparatus, in particular an x-ray computed tomography apparatus, of the type having at least a first acquisition system (with a first radiator and a first detector for detection of the radiation originating from the first radiator) and a second acquisition system (comprising a second radiator and a second detector for detection of the radiation originating from the second radiator), wherein both acquisition systems are capable of rotating around a common rotation axis.

2. Description of the Prior Art

Tomography apparatuses of the above type are known from U.S. Pat. Nos. 4,991,190; 4,384,359; 4,196,352; 5,966,422 and 6,421,412. An advantage that such tomography apparatuses with multiple acquisition systems exhibit in comparison to a device with one acquisition system is an increased data acquisition rate, which leads to a shorter exposure time, and/or to an increased temporal resolution. A shortened exposure time is of advantage because with it, movement artifacts in the reconstructed image (for example, caused by voluntary and involuntary movements of the patient and/or by arrhythmias in the heart movement) are minimized. This is particularly of importance in the event a larger volume is scanned, for example by means of a spiral scan, such as of the heart. An increased temporal resolution is necessary for representation of, for example, movement cycles, because then the data used for reconstruction of an image must be acquired in the shortest possible time. Conventionally, this has been attempted to be achieved by increasing the rotation speed of the acquisition system, but the acceleration forces, and the mechanical problems resulting therefrom, increase significantly with additional rotation speed. Such problems can be solved aforementioned tomography devices, which have multiple acquisition systems (radiator-detector combinations) arranged separated from one another in the azimuthal direction, meaning "angularly offset" opposite one another. The aforementioned tomography devices are particularly advantageous for the case when such spiral reconstruction algorithms are used for reconstruction of images from the raw data generated by the detectors, which only require projection data from an angular interval of 180°, because then given the presence of, for example, two acquisition systems, the exposure time is reduced to a quarter of the measurement time required for a full rotation.

SUMMARY OF THE INVENTION

An object of the present invention is to expand the functionality of a tomography device of the aforementioned type.

This object is achieved according to the invention in a tomography apparatus of the type initially described, wherein the maximum measurement fields sampled by the two acquisition systems given rotation around the rotation axis are of different sizes (i.e., respective sizes that differ from each other), and/or wherein the measurement fields of the two acquisition systems can be adjusted to different sizes (i.e., respective sizes that differ from each other).

Both acquisition systems preferably are capable of rotating around the common rotation axis with a constant angular separation in the azimuthal direction.

For example, the smaller (maximum) measurement field can exhibit a cross-sectional area of 60% or less, in particular 45% or less, or 25% or less in comparison to the larger (maximum) measurement field.

The invention is based on the recognition that typically projection data from a full rotation (360°) of the x-ray radiator are used for reconstruction of a CT image, but given use of n radiator-detector pairs, in particular disposed in a plane, the time to acquire a 360° data set can be reduced by the factor 1/n. However, since the detector mountings or detector arms, as well as, if present, radiator gating devices, must not shadow one another, n can not be selected arbitrarily large without significantly restricting the maximum possible fan angle, and therewith the measurement field of all individual radiator-detector combinations of each acquisition system. For n=3, the measurement field of a tomography device with three identical acquisition systems already would be significantly restricted in comparison to a tomography device with only one acquisition system, and, given n=2, there can also be restrictions in the possible measurement field size in tomography devices with small focus rotation axis separation.

A measurement field that is too severely restricted can mean that a sub-region of a body slice (namely, for example, the sub-region containing the human heart) can be scanned with high quality, but a scanning of the entire body cross-section, and thus the acquisition of an entire body section image (slice), can no longer be possible.

The invention is based on the recognition that very short exposure times are, for the most part, necessary only for representation of the human heart or other moving organs of the person, and that only a small measurement field is necessary for such representation of the human heart.

The problem of the measurement field being too severely restricted can be solved by a combination of a radiator-detector combinations that covers the entire measurement field with one or more radiator-detector combinations that each cover only a limited measurement field. For example, an image is thereby obtained of the whole body cross-section with normal temporal resolution, and a representation of the heart region is obtained with increased temporal resolution. The number of the possible acquisition systems or radiator-detector combinations depends on the special device geometry and the desired actual measurement field. The tomography device is also advantageous for examination of inanimate items, for example luggage, because it allows both a larger region and a smaller region to be scanned with high quality.

The region that can be scanned by an acquisition system, provided for the examination subject (in particular the patient), is characterized as a measurement field, from which projection data sufficient for an image reconstruction are generated in a half or complete rotation. The measurement fields of the two acquisition systems are normally circular or given a simultaneous (successive or continuous) feed in the z-direction, cylindrical, and normally lie concentrically one atop the other or one in the other.

The two acquisition systems for acquisition of projection data preferably are arranged to obtain data from a number of different projection directions. In particular, both acquisition systems are fashioned for generation of slice exposures and/or for 3D scanning of the examination subject.

According to a preferred embodiment, the maximum fan angle of both acquisition systems are of different sizes, and/or the fan angle of both acquisition systems can be set to different sizes.

The x-ray radiation emitted from a conventional x-ray tube as an x-ray beam is normally emitted in an angular range of 360°. The radiation incident on the associated x-ray detector can contribute to the image generation. The image-relevant x-ray radiation beam is defined in a plane perpendicular to the rotation axis (meaning in the slice plane) by the fan angle. This is not to be confused with what is known as the conical angle, which describes the expansion of the x-ray radiation beam in the z-direction and which, in particular given the advantageous embodiment also considered here of the detectors being multi-line detectors or as what are known as surface detectors, can absolutely reach considerable values, such that this can no long be neglected in the image reconstruction.

From the above, it arises that the maximum fan angle of an acquisition system output system, normally determined substantially by the length of the appertaining x-ray detector (which is preferably curved around the focus of the x-ray radiator), is measured in the azimuthal direction. Thus the lengths of both detectors are preferably of different sizes, measured in the azimuthal direction. Given use of detector elements of the same size in both detectors, this means that many different detector elements (for example 672 elements or 336 elements) are present in the two detectors.

For example, the smaller maximum fan angle or the small detector length exhibits a value of 75% or less, or 50% or less, or of 25% or less with regard to the corresponding value of the large acquisition system.

With particular advantage, the first measurement field is arranged for scanning the entire body cross-section of the patient, and the second measurement field is arranged for scanning a part of the body cross-section of the patient, in particular of the region of the heart.

According to another preferred embodiment, the detector of each acquisition systems has a number of detector elements proceeding in succession in the azimuthal direction, with the detector elements of the first detector exhibiting the same element separation from one another as the detector elements of the second detector.

Among other things, in this embodiment the detectors are particularly advantageously mounted on the respective acquisition system, such that after a common rotation of both acquisition systems (which transfers an imaginary connecting line "first focus of the first radiator—rotation center" to the previous position of an imaginary connecting line "second focus of the second radiator—rotation center"), at least some of the detector elements of the first detector come to lie at a displacement angle, for example equal to the half element separation, displaced with regard to the previous positions of the detector elements of the second detector. This has the advantage that a finer scanning of the examination subject or patient ensues that corresponds in effect to what is known as a springing focus. Scanning errors are thereby minimized. This preferred embodiment is also of advantage in a tomography device with two or more acquisition systems with an identical fan angle or measurement field.

The aforementioned "springing focus substitution" is in particular dealt with according to the rule that the difference of two angular positions is a whole-number, odd multiple of the half-element separation, with the angular positions are defined as follows:

a) an angular position of a detector element of the first detector, measured around the first focus between the imaginary connecting line "first focus—rotation center" and an imaginary connecting line "first focus—detector element", and b) an angular position of a detector element of the second detector, measured around the second focus between the imaginary connecting line "second focus—rotation center" and an imaginary connecting line "second focus—detector element".

Preferably, in the tomography device according to the invention, both acquisition systems are arranged in a common plane. From this in particular, the advantage arises of an increased temporal resolution in the representation of movement cycles in comparison to known systems.

The invention also encompasses an embodiment wherein both acquisition systems are separated from one another in the direction of the rotation axis, and/or can be positioned separated from one another in the direction of the rotation axis. This preferred embodiment is particularly advantageous when the exposure of a large volume should ensue in the shortest possible time without pauses for cooling of the radiator. The axial separation of the two acquisition systems is thereby equal to that of the subject region scanned by an acquisition system in the axial direction, meaning in the direction parallel to the rotation axis, or to a whole-number multiple thereof. This means that if both acquisition systems are displaced from one another by a separation d in the axial direction, a region 2d is scanned in a scan region or traversal path d of the patient positioning device.

For minimization of the radiation dosage, preferably an arrangement to minimize the radiation, associated with the acquisition system with the larger maximum measurement data, is present in the region of the larger measurement field, and in which region the larger measurement field does not overlap with the smaller measurement field of the other acquisition system. For example, an unnecessary radiation exposure in the region outside of the human heart can thereby be reduced or prevented, in the event that only the head should be scanned.

Such an arrangement can be, for example, a gating device with which the fan angle of the acquisition system with the large measurement field can be decreased, in particular can be continuously decreased.

The arrangement can alternatively be a filter device that, for example, has two different filters that can selectively be introduced into the radiation beam, one of filters exhibiting a lower radiation transparency in the region of the larger measurement field, in which the larger measurement field does not overlap with the smaller measurement field, than the other filter in the same region.

According to a preferred embodiment, the tomography device has a control device or control unit that is fashioned such that a selection can be made, at least between a first scanning mode with large measurement field and a second scanning mode with small measurement field, by an operating personnel, for example by a doctor or by a medical-technical assistant. For example, the first scanning mode can be designed for scanning the entire body cross-section of a patient, and the second scanning mode can be designed for scanning only the heart region.

In the first scanning mode, the acquisition system with the smaller measurement field is preferably inactive, meaning, for example, that the associated radiator is deactivated.

In turn, in the second scanning mode both acquisition systems are preferably active. For example, in the second scanning mode the fan angle of the acquisition system with the larger measurement field is made smaller by the gating device, and/or a more strongly absorbing filter is introduced into the outer region.

According to another preferred embodiment, a control and/or imaging computer (that can also be present to control the radiator) is fashioned such that the image reconstruction is implemented differently depending on the selected scanning mode. For example, in the first scanning mode a reconstruction algorithm for an individual acquisition system is applied, and in the second scanning mode a special algorithm for a number of scanning systems is applied.

According to another preferred embodiment, the control and/or the imaging computer is fashioned such that raw data can be used by both acquisition systems for image reconstruction, in particular for reconstruction of the same image.

DESCRIPTION OF THE PREFERRED EMBODIMENTS

Two exemplary embodiments of a tomography apparatus according to the invention are subsequently explained in detail using FIGS. 1 through 4.

Figure 1:
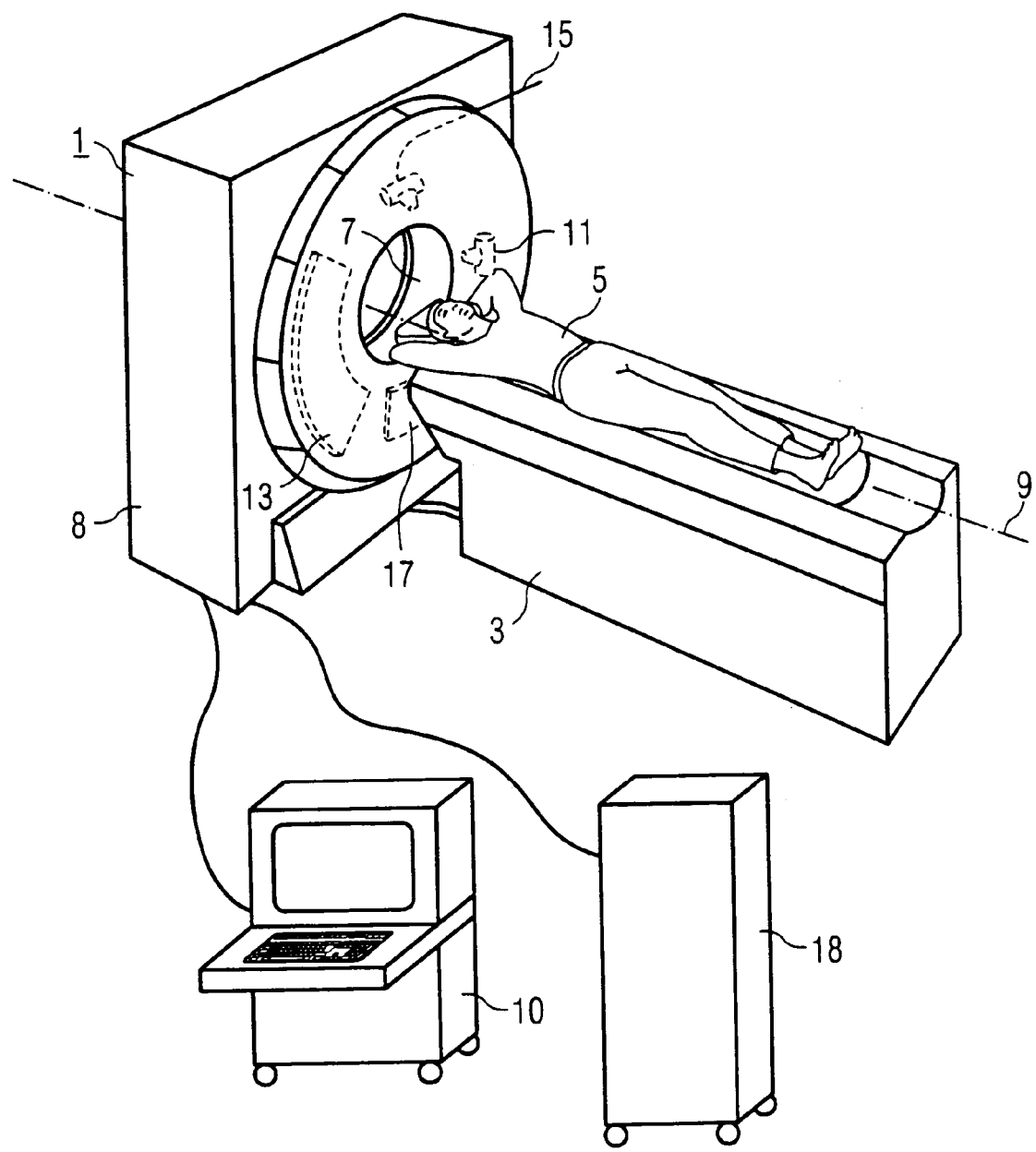
FIG. 1 is a first exemplary embodiment of a tomography apparatus according to the invention in a perspective view.

FIG. 1 shows a tomography apparatus 1 (here an x-ray computed tomography apparatus) with an associated positioning device 3 for exposure and positioning of a patient 5. The patient 5 with the desired examination region or scan region can be inserted into an opening 7 (diameter 70 cm) in the housing 8 of the tomography device 1 by means of a movable table top of the positioning device 3. Moreover, in the case of a spiral scan, a continuous axial feed is effected with the positioning device 3.

Inside the housing 8, a gantry (not visible in FIG. 1) can be rotated with high speed around a rotation axis 9 running through the patient 5.

An operating unit 10 is present for operation of the tomography device 1 by a doctor or the like.

To achieve a short scan time and/or a high temporal resolution, a number of acquisition systems, for example two acquisition systems (n=2) are mounted on the gantry. A first acquisition system has an x-ray tube as a first radiator 11 and an eight-line x-ray detector array as a first detector 13. A second acquisition system has a separate x-ray tube as a second radiator 15 and a separate eight-line x-ray detector array as a second detector 17. The arrangement of the two radiators 11, 15 and of the two detectors 13, 17 on the gantry is fixed during the operation of the tomography device 1, such that their relative separations are also constant during the operation.

The x-ray detector arrays are fashioned on a base of an electronically readable scintillator ceramic, known as a UFC ceramic. Surface detectors, for example with 256 or more lines, can also be used.

The projection data of both continuously scanning acquisition systems are processed into a CT image in a control and/or imaging computer 18, using an image reconstruction algorithm.

Figure 2:
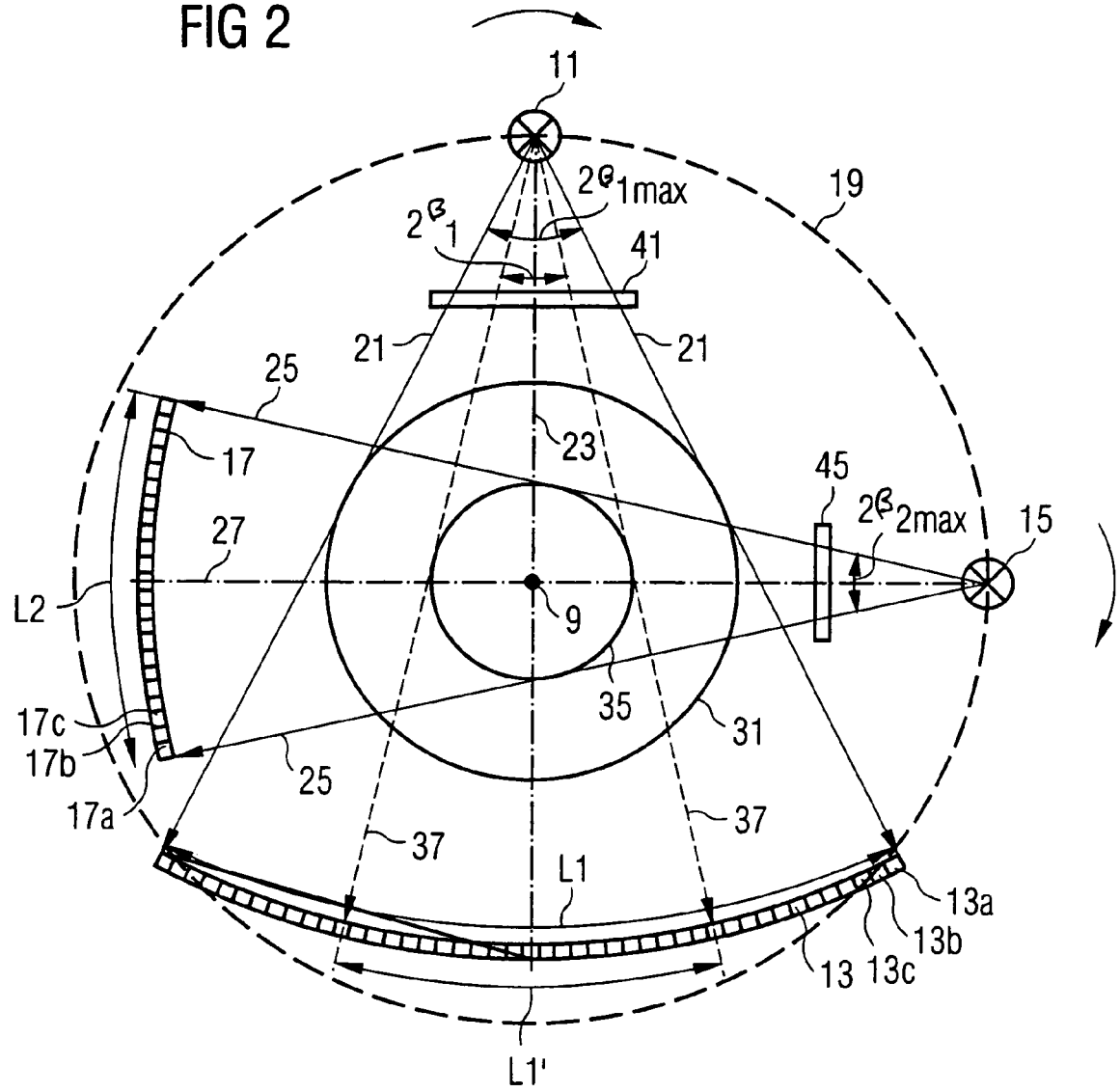
FIG. 2 shows two acquisition systems of the tomography apparatus of FIG. 1 in cross-section view.

FIG. 2 shows both acquisition systems in detail. It is in particular shown how the two radiators 11, 15 rotate on a common rotation path 19 around the rotation axis 9 in the direction of the arrow, while raw data are generated from different projection angles for a subsequent image reconstruction. In the cross-section of FIG. 2, one line of the detectors 13 or 17 is shown with a number of detector elements 13a, 13b, 13c or 17a, 17b, 17c . . . The detector pitch of both detectors 13, 17 is identical.

The lengths L1 and L2 of the respective detectors 13 and 17 are curved around the respective focus of the associated radiator 11 or 15 and are different, such that, in the representation of FIG. 2, detectable x-ray beams of different sizes exist for the two acquisition systems. For image generation, the first acquisition system can use an x-ray beam with edge rays 21, a middle ray 23, and with a maximum fan angle $2\beta_{1max}$ of approximately 55°. Correspondingly, the second acquisition system can use an x-ray beam with edge rays 25, a middle ray 27, and with a maximum fan angle $2\beta_{2max}$ of approximately 25°. Due to the rotary scanning by both measurement systems, a maximum measurement field 31 of approximately 50 cm diameter arises for the first measurement system, and a comparably smaller maximum measurement field 35 of only 25 cm diameter arises for the second acquisition system.

The first measurement field 31 is designed to scan the entire body cross-section of the patient 5, and the second measurement field 35 is designed to scan only the heart region of the patient.

Operating personnel can select, among other things, the following operating modes through the operating unit 10:

In a body-operating mode of the tomography device 1, raw data are acquired by the first acquisition system for the subsequent image reconstruction from the first measurement field 31. The second acquisition system, and in particular the second radiator 15, can be inactive in this mode. The entire body cross-section of the patient 5 is then scanned with conventional temporal resolution.

In a heart-operating mode of the tomography device 1 according to the invention, raw data are acquired by both acquisition systems. In this mode, the second measurement field 35 is scanned with increased temporal resolution and/or with increased data rate in comparison to a device with only one acquisition system. The first detector 13 is thereby used only with a length L1' (shortened in comparison to its overall length L1) that is substantially identical to the length L2 of the smaller detector 17. The x-ray radiation incident in the annular region between the two borders of the measurement fields 31, 35 thus possibly passes the patient 5 unused. As needed, it may be, of advantage to adjust the current fan angle $2\beta_1$ of the first acquisition system in the heart operating mode to a value smaller than the maximum fan angle $2\beta_{1max}$ of the first acquisition system, in particular identical to the maximum fan angle $2\beta_{2max}$ of the second acquisition system. Corresponding edge rays are indicated in FIG. 2.

To gate the x-ray beam emanating from the radiators 11 or 15 in the direction of the rotation axis, thus also to select individual or multiple detector lines, a first gating device 41 is associated with the first acquisition system, and a second gating device 45 is associated with the second acquisition system, proximate the respective radiators 11 and 15. Each gating device 41, 45 can have, for example, two diaphragm plates that can be moved in a direction parallel to the rotation axis 9.

To aid the adjustment of fan angles of different sizes, in particular to reduce the fan angle of the first acquisition system to a value $2\beta_1$ defined by edge rays 37, a radiation minimization device 51 (schematically indicated in FIG. 3) is present to minimize the radiation in the ring region between the two measurement field boundaries. The device 51 is, for example, a further gating device, present in addition to the first gating device 41, with schematically indicated diaphragm plates 52, 53 that can be moved in the direction perpendicular to the rotation axis 9 (meaning in the slice plane) (double arrow 54). Alternatively or additionally, the device 51 can be fashioned as a filter device 55, or can include such a device. Two different filters 56, 57, one for the body operation mode and the other for the heart operation mode, are schematically indicated.

Figure 3:
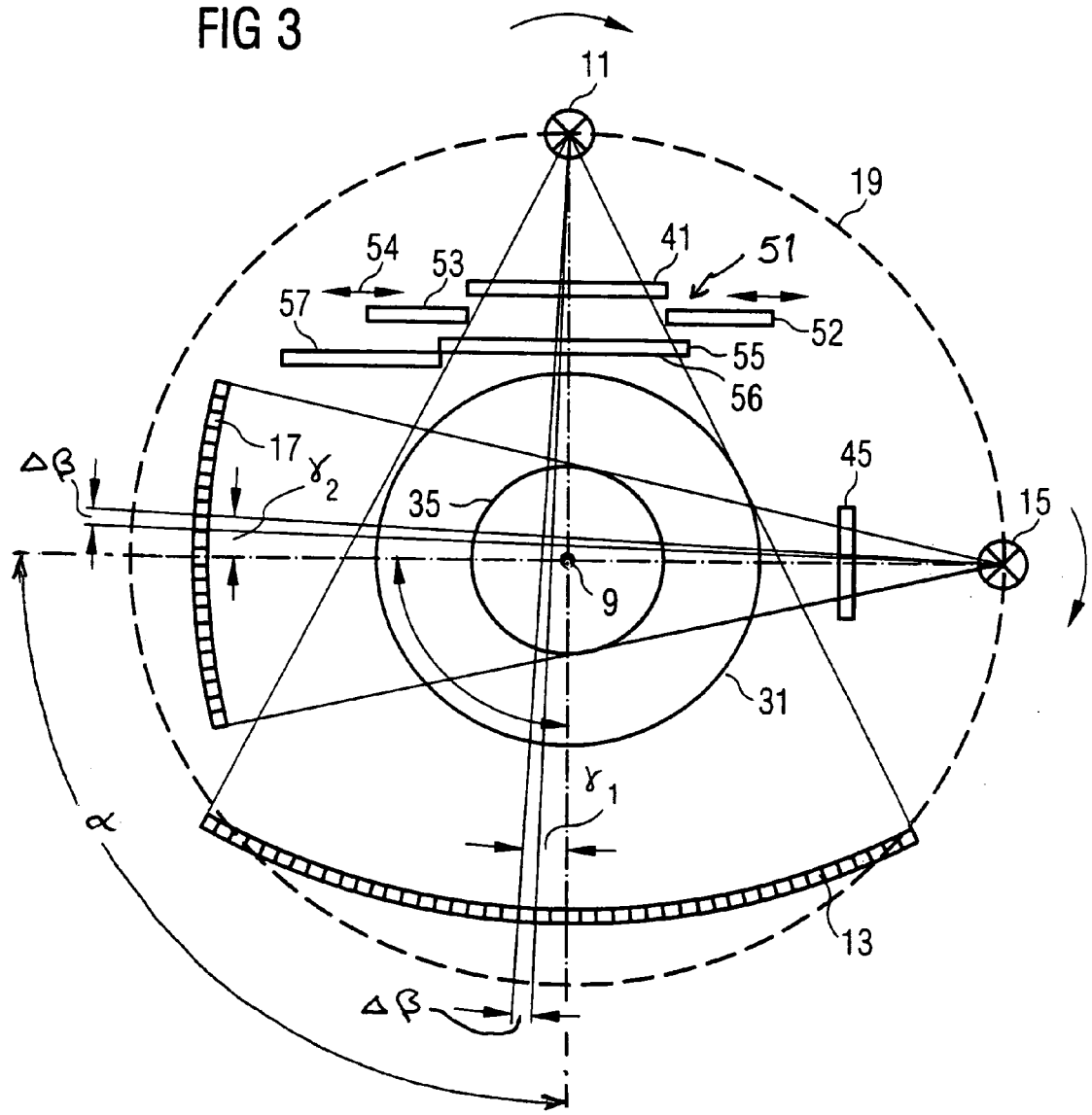
FIG. 3 shows other details of the embodiment of FIG. 2.

In FIG. 3, a further feature of the tomography device 1 is shown. It concerns the azimuthal separation of the two acquisition systems (indicated in FIG. 3 with the angles $\gamma_1$, $\gamma_2$ and $\alpha$, or, formulated differently, the azimuthal separation of two arbitrary detector elements of the detectors 13 or 17. In FIG. 3, the equidistant detector pitch (identical for both acquisition systems) or the identical, equidistant element separation $\Delta\beta$ is indicated.

The position of each of the acquisition systems is defined in the following by an imaginary connecting line "first focus of the first radiator 11—rotation center on the rotation axis 9" or "second focus of the second radiator 15—rotation center on the rotation axis 9". In the example, these lines are identical to the middle rays 23 or 27 (FIG. 2).

The—constant at least during the exposure—azimuthal angular separation a of the acquisition systems is, given a number n of acquisition systems, preferably substantially 360°/(2n), meaning in the example of the Figures (n=2), substantially 90°, such that after 1/(2n) of a complete rotation circuit (360°) an angular region of 180° is cumulatively scanned, which is sufficient for most of the subsequent image reconstruction algorithms. In the context of the invention, preferably a spiral reconstruction algorithm is used, that functions by with projection data of a half-rotation.

The detector 13 of the first acquisition system is installed, relative to the connecting line "first focus—rotation center", displaced in the azimuthal direction by a whole-number, odd multiple of the half-element separation $\Delta\beta$ or of the half detector pitch in comparison to the second acquisition system. The most advantageous case is a displacement by $\Delta\beta/2$.

With regard to the individual detector elements, an analogous installation rule can be established. For this, $\gamma_4$ the angular position of an arbitrary detector element 13a, 13b, 13c, . . . of the first detector 13, measured at the first focus between the imaginary connecting line "first focus—rotation center" and an imaginary connecting line "first focus—detector element 13a, 13b, 13c, . . . ", and $\gamma_2$ the angular position of an arbitrary detector element 17a, 17b, 17c, . . . of the first detector 17, measured at the second focus between the imaginary connecting line "second focus—rotation center"and an imaginary connecting line "second focus—detector element 17a, 17b, 17c, . . . ".

The respective positions of the detector elements 13a, 13b, 13c, . . . , 17a, 17b, 17c, . . . are respectively measured from the element edge side in FIG. 3.

Both detectors 13, 17 are installed such that the difference $\gamma_1-\gamma_2$ of the two angular positions $\gamma_1$, $\gamma_2$ is a whole-number, odd multiple 2N+1 of the half element separation $\Delta\beta$:

$$\gamma_1 - \gamma_2 = (2N+1) \cdot \frac{\Delta\beta}{2}, \text{ with } N = 0, 1, 2, 3 \quad \text{[Equation 1]}$$

This installation rule results in, after a rotation of the gantry by the angular separation $\alpha$, the elements 13a, 13b, 13c, . . . of the first detector 13 coming to lie displaced to the position of the elements 17a, 17b, 17c, . . . of the second detector 17 before the rotation.

This allows a particularly highly resolved scanning of the patient 5 from particularly many different projection directions.

In the exemplary embodiment of the tomography device according to FIGS. 1 through 3, both acquisition systems (meaning the respective connecting lines between radiator and detector, thus for example also the respective middle rays 23 and 27) are arranged in a common plane, which is the drawing plane of FIGS. 2 and 3. The first exemplary embodiment is particularly suited for representation of movement cycles with high temporal resolution.

Figure 4:
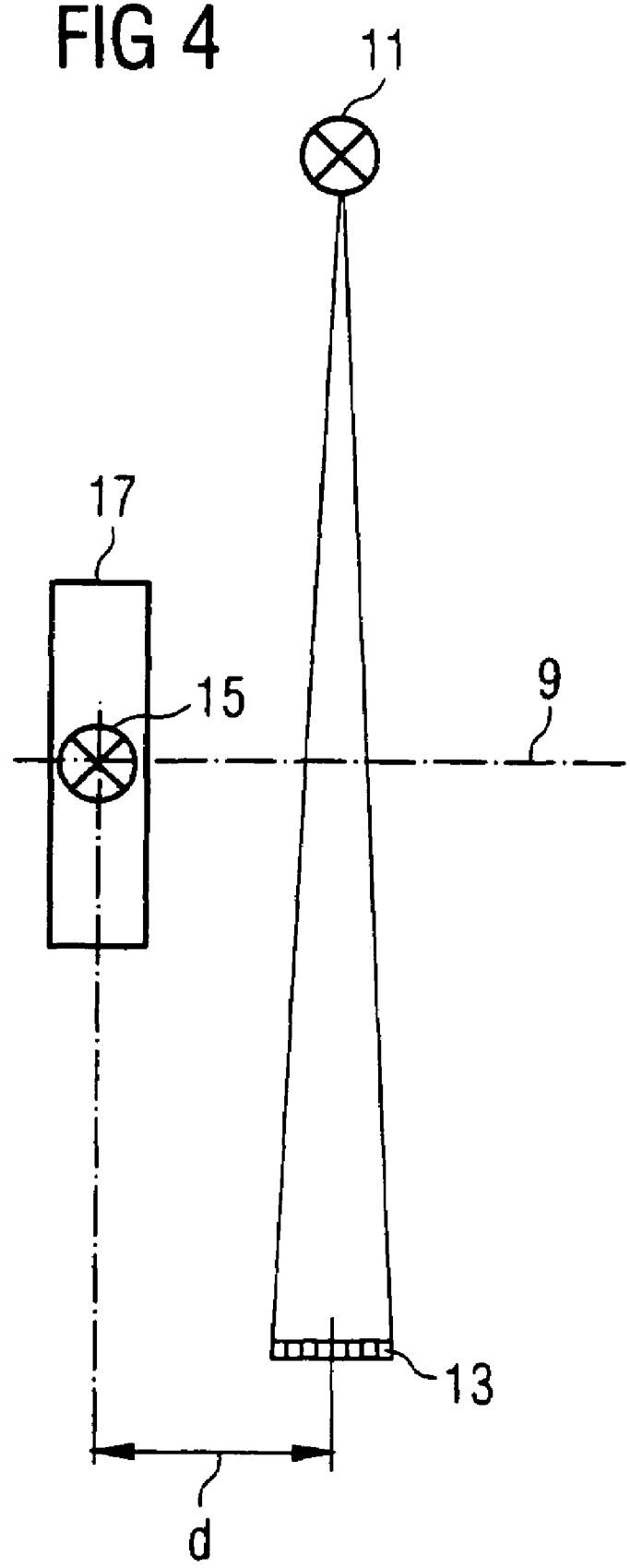
FIG. 4 shows both acquisition systems of a tomography apparatus according to a second exemplary embodiment, in a longitudinal section view.

FIG. 4 shows a second exemplary embodiment of the tomography device 1 that is substantially identical to the exemplary embodiment according to FIGS. 1 through 3, but with the difference that both acquisition systems are separated from one another by a distance d in the direction of the rotation axis 9. Such a characteristic is of advantage in order to be able to acquire as large a volume as possible in the shortest possible time without cooling pauses of the radiators 11, 15.

In an alternative exemplary embodiment, the tomography device according to FIGS. 1 through 3 can be brought from a planar mode into a mode with axial displacement, and vice versa, via a relative movement of the acquisition systems in the axial direction.

Although tomography devices with two acquisition systems are shown in the exemplary embodiments, the inventive concept also is applicable to tomography devices with three or more acquisition systems. The invention thus also encompasses tomography devices with three acquisition systems, wherein two of the acquisition systems exhibit a small, equally large measurement field, and where a third of the acquisition systems provides a larger measurement field in comparison to this. Tomography devices are also possible in which, of at least three acquisition systems, three measurement fields different from one another are made available.

Although modifications and changes may be suggested by those skilled in the art, it is the intention of the inventors to embody within the patent warranted hereon all changes and modifications as reasonably and properly come within the scope of their contribution to the art.

We claim as our invention:

1. An imaging tomography apparatus comprising:
 a first data acquisition system comprising a first radiator and an arcuate first detector for detecting radiation originating from said first radiator;
 a second data acquisition system comprising a second radiator and an arcuate second detector for detecting radiation originating from said second radiator;
 a gantry to which said first data acquisition system and said second data acquisition system are mounted for rotation around a common rotation axis;
 said first detector having a first length measured in an azimuthal direction relative to said common rotation axis, and said second detector having a second length measured in said azimuthal direction, said first length and said second lengths being different; and during rotation around said common rotation axis, said first data acquisition system and said second data acquisition system respectively scanning maximum measurement fields that differ in size from each other, with said first data acquisition system generating a first set of computed tomography projection data, and wherein said second data acquisition system generating a second set of computed tomography projection data.

2. An imaging tomography apparatus as claimed in claim 1 wherein said first radiator is a first x-ray radiator, and said first detector is a first detector is a first x-ray detector.

3. An imaging tomography apparatus as claimed in claim 1 wherein said first radiator emits a radiation beam having a maximum fan angle and wherein said second radiator emits a radiation beam having a maximum fan angle, the maximum fan angle of said first radiation beam being different from the maximum fan angle of the second radiation beam.

4. An imaging tomography apparatus as claimed in claim 1 wherein each of said first data acquisition system and said second data acquisition system is adapted to scan a patient, said patient having a body cross-section, and wherein said maximum measurement field of said first data acquisition system has a size for scanning an entirety of said body cross-section of the patient, and wherein said maximum measurement field of said second data acquisition system has a size for scanning only a part of said body cross-section of the patient.

5. An imaging tomography apparatus as claimed in claim 4 wherein said maximum measurement field of said second data acquisition system has a size for scanning only a part of said body cross-section of said patient containing the heart.

6. An imaging tomography apparatus as claimed in claim 1 wherein each of said first detector and said second detector is comprised of a plurality of detector elements disposed in succession in an azimuthal direction relative to said common rotation axis, and wherein the detector elements of said first detector have an element separation between successive detector elements that is equal to an element separation between the respective detector elements of the second detector.

7. An imaging tomography apparatus as claimed in claim 6 wherein said first radiator has a first focus from which radiation from said first radiator emanates, and wherein said second radiator has a second focus from which radiation from said second radiator emanates, and wherein said first data acquisition system and said second data acquisition system are mounted so that, when said first and second data acquisition systems are rotated to cause a line proceeding from said first focus to said common rotation axis to occupy a previous position of a line proceeding between said second focus and said common rotation axis, at least some of the detector elements of the first detector are displaced by a displacement angle relative to respective locations of at least some of the detector elements of the second detector at said previous position.

8. An imaging tomography apparatus as claimed in claim 7 wherein each detector element of said first detector exhibits a first angular position, measured from said line proceeding between said first focus and said common rotation axis and a line proceeding between said first focus and that detector element of the first detector, and wherein each detector element of said second detector exhibits a second angular position, measured between said line proceeding between said second focus and said common rotation axis and a line proceeding between said second focus and that detector element of the second detector, and wherein a difference between said first angular position and said second angular position is an odd whole-number multiple of ½ of said element separation.

9. An imaging tomography apparatus as claimed in claim 1 wherein said first data acquisition system and said second data acquisition system are mounted in a common plane.

10. An imaging tomography apparatus as claimed in claim 1 wherein said first data acquisition system and said second data acquisition system are mounted so as to be separated from each other, in respective planes, along said common rotation axis.

11. An imaging tomography apparatus as claimed in claim 1 wherein at least one of said first and second data acquisition systems is mounted so as to be movable relative to the other of said first and second data acquisition systems along said common rotation axis, to cause said first and second data acquisition systems to be respectively disposed in different planes.

12. An imaging tomography apparatus as claimed in claim 1 wherein one of said first and second data systems has a larger maximum measurement field and the other of said first and second data acquisition systems has a smaller maximum measurement field, and comprising an operating unit, connected to said first and second data acquisition systems, for allowing a selection to be made between a first scanning mode with said larger maximum measurement field and a second scanning mode with said smaller maximum measurement field.

13. An imaging tomography apparatus as claimed in claim 12 wherein said operating unit, in said first scanning mode, deactivates the data acquisition system having said smaller maximum measurement field.

14. An imaging tomography apparatus as claimed in claim 12 wherein, in said second scanning mode, said operating unit activates both said first and second data acquisition systems.

15. An imaging tomography apparatus:
a first data acquisition system comprising a first radiator and a first detector for detecting radiation originating from said first radiator;
a second data acquisition system comprising a second radiator and a second detector for detecting radiation originating from said second radiator;
a gantry to which said first data acquisition system and said second data acquisition system are mounted for rotation around a common rotation axis;
one of said first and second data acquisition systems having a larger maximum measurement field and the other of said first and second data acquisition systems has a smaller maximum measurement field;
during rotation around said common rotation axis, said first data acquisition system and said second data acquisition system respectively scanning maximum measurement fields that differ in size from each other, each of said first and second data acquisition systems generating raw data resulting from scanning;
an operating unit, connected to said first and second data acquisition systems, for allowing a selection to be made between a first scanning mode with said larger maximum measurement field and a second scanning mode with said smaller maximum measurement field; and
a computer supplied with said raw data for reconstructing an image therefrom, said computer being connected to said operating unit and reconstructing said image differently dependent on whether said first scanning mode or said second scanning mode is selected.

16. An imaging tomography apparatus as claimed in claim 15 wherein said computer, in at least one of said first and second scanning modes, reconstructs a single image using the raw data from both of said first and second data acquisition systems.

17. An imaging tomography apparatus comprising:
a first data acquisition system comprising a first radiator and an arcuate first detector for detecting radiation originating from said first radiator for scanning a first measurement field;
a second data acquisition system comprising a second radiator and an arcuate second detector for detecting radiation originating from said second radiator for scanning a second measurement field;
a gantry to which said first data acquisition system and said second data acquisition system are mounted for rotation around a common rotation axis;
said first detector having a first length measured in an azimuthal direction relative to said common rotation axis, and said second detector having a second length measured in said azimuthal direction, said first length and said second lengths being different; and
a setting arrangement for, during rotation around said rotation axis, setting the measurement field for at least one of said first data acquisition system and said second data acquisition system so that the respective measurement fields differ in size from each other, with said first data acquisition system generating a first set of computed tomography projection data, and wherein said second data acquisition system generating a second set of computed tomography projection data.

18. An imaging tomography apparatus as claimed in claim 17 wherein said first radiator is a first x-ray radiator, said first detector is a first detector is a first x-ray detector, said second radiator is a second x-ray radiator and said second detector is a second x-ray detector.

19. An imaging tomography apparatus as claimed in claim 17 wherein said first radiator emits a radiation beam having a fan angle and wherein said second radiator emits a radiation beam having a fan angle, the fan angle of said first radiation beam being different from the fan angle of the second radiation beam.

20. An imaging tomography apparatus as claimed in claim 17 wherein each of said first data acquisition system and said second data acquisition system is adapted to scan a patient, said patient having a body cross-section, and wherein said measurement field of said first data acquisition system has a size for scanning an entirety of said body cross-section of the patient, and wherein said measurement field of said second data acquisition system has a size for scanning only a part of said body cross-section of the patient.

21. An imaging tomography apparatus as claimed in claim 20 wherein said measurement field of said second data acquisition system has a size for scanning only a part of said body cross-section of said patient containing the heart.

22. An imaging tomography apparatus as claimed in claim 17 wherein each of said first detector and said second detector is comprised of a plurality of detector elements disposed in succession in an azimuthal direction relative to said common rotation axis, and wherein the detector elements of said first detector have an element separation between successive detector elements that is equal to an element separation between the respective detector elements of the second detector.

23. An imaging tomography apparatus as claimed in claim 22 wherein said first radiator has a first focus from which radiation from said first radiator emanates, and wherein said second radiator has a second focus from which radiation from said second radiator emanates, and wherein said first data acquisition system and said second data acquisition system are mounted so that, when said first and second data acquisition systems are rotated to cause a line proceeding from said first focus to said common rotation axis to occupy a previous position of a line proceeding between said second focus and said common rotation axis, at least some of the detector elements of the first detector are displaced by a displacement angle relative to respective locations of at least some of the detector elements of the second detector at said previous position.

24. An imaging tomography apparatus as claimed in claim 23 wherein each detector element of said first detector exhibits a first angular position, measured from said line proceeding between said first focus and said common rotation axis and a line proceeding between said first focus and that detector element of the first detector, and wherein each detector element of said second detector exhibits a second angular position, measured between said line proceeding between said second focus and said common rotation axis and a line proceeding between said second focus and that detector element of the second detector, and wherein a difference between said first angular position and said second angular position is an odd whole-number multiple of ½ of said element separation.

25. An imaging tomography apparatus as claimed in claim 17 wherein said first data acquisition system and said second data acquisition system are mounted in a common plane.

26. An imaging tomography apparatus as claimed in claim 17 wherein said first data acquisition system and said second data acquisition system are mounted so as to be separated from each other, in respective planes, along said common rotation axis.

27. An imaging tomography apparatus as claimed in claim 17 wherein at least one of said first and second data acquisition systems is mounted so as to be movable relative to the other of said first and second data acquisition systems along said common rotation axis, to cause said first and second data acquisition systems to be respectively disposed in different planes.

28. An imaging tomography apparatus as claimed in claim 17 wherein one of said first and second data acquisition systems has a larger maximum measurement field and the other of said first and second data acquisition systems has a smaller maximum measurement field, and wherein said setting arrangement is associated with said one of said data acquisition systems having said larger maximum measurement field, and is disposed to interact with said larger maximum measurement field to reduce said larger maximum measurement field to form said measurement field of said one of said data acquisition systems, so that said measurement field of said one of said data acquisition systems does not overlap said measurement field of said other of said data acquisition systems.

29. An imaging tomography apparatus as claimed in claim 28 wherein said setting arrangement is a gating device disposed to interact with said radiation originating from the radiator of said one of said data acquisition systems having said larger maximum measurement field, to set and reduce a fan angle of said radiation.

30. An imaging tomography apparatus as claimed in claim 29 wherein said gating device has movable diaphragm plates, movable toward and away from each other, to selectively set said fan angle.

31. An imaging tomography apparatus as claimed in claim 28 wherein said setting arrangement is a filter device.

32. An imaging tomography apparatus as claimed in claim 31 wherein said filter device comprises a plurality of filters selectively introducible into said radiation, said plurality of filters respectively having differing radiation transparencies in a region of said measurement field of one of said data acquisition systems which does not overlap with said measurement field of said other of said data acquisition systems.

33. An imaging tomography apparatus as claimed in claim 17 wherein one of said first and second data systems has a larger measurement field and the other of said first and second data acquisition systems has a smaller measurement field, and comprising an operating unit, connected to said first and second data acquisition systems, for allowing a selection to be made between a first scanning mode with said larger measurement field and a second scanning mode with said smaller measurement field.

34. An imaging tomography apparatus as claimed in claim 33 wherein said operating unit, in said first scanning mode, deactivates the data acquisition system having said smaller measurement field.

35. An imaging tomography apparatus as claimed in claim 33 wherein, in said second scanning mode, said operating unit activates both said first and second data acquisition systems.

36. An imaging tomography apparatus comprising:
  a first data acquisition system comprising a first radiator and a first detector for detecting radiation originating from said first radiator for scanning a first measurement field to generate raw data;
  a second data acquisition system comprising a second radiator and a second detector for detecting radiation originating from said second radiator for scanning a second measurement field for generating raw data;
  a gantry to which said first data acquisition system and said second data acquisition system are mounted for rotation around a common rotation axis;
  a setting arrangement for, during rotation around said rotation axis, setting the measurement field for at least one of said first data acquisition system and said second data acquisition system so that the respective measurement fields differ in size from each other, with one of said first and second acquisition systems having a laraer measurement field and the other of said first and second data acquisition systems having a smaller measurement field;
  an operating unit, connected to said first and second data acquisition systems, for allowing a selection to be made between a first scanning mode with said larger maximum measurement field and a second scanning mode with said smaller maximum measurement field; and
  a computer supplied with said raw data for reconstructing an image therefrom, said computer being connected to said operating unit and reconstructing said image differently dependent on whether said first scanning mode or said second scanning mode is selected.

37. An imaging tomography apparatus as claimed in claim 36 wherein said computer, in at least one of said first and second scanning modes, reconstructs a single image using the raw data from both of said first and second data acquisition systems.

* * * * *